United States Patent
Heil, Jr.

(10) Patent No.: US 7,530,989 B2
(45) Date of Patent: May 12, 2009

(54) ENDOCARDIAL SPLINT AND METHOD THEREFOR

(75) Inventor: Ronald W. Heil, Jr., Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 11/870,324

(22) Filed: Oct. 10, 2007

(65) Prior Publication Data

US 2008/0033236 A1 Feb. 7, 2008

Related U.S. Application Data

(63) Continuation of application No. 10/877,905, filed on Jun. 25, 2004, now Pat. No. 7,288,104.

(51) Int. Cl.
*A61B 17/08* (2006.01)
*A61F 1/00* (2006.01)

(52) U.S. Cl. .......................... 606/213; 600/37

(58) Field of Classification Search ......... 128/897–899; 600/16–18, 37; 602/5, 16; 604/11, 13, 15, 604/174–175; 606/151, 153, 213, 215, 220; 607/119, 129; 623/2.1, 2.11, 11.11, 66.1
See application file for complete search history.

(56) References Cited

U.S. PATENT DOCUMENTS

| | | | |
|---|---|---|---|
| 5,855,614 A | 1/1999 | Stevens et al. |
| 6,260,552 B1 | 7/2001 | Mortier et al. |
| 6,406,420 B1 | 6/2002 | McCarthy et al. |
| 6,428,537 B1 | 8/2002 | Swanson et al. |
| 6,616,684 B1 | 9/2003 | Vidlund et al. |
| 6,990,370 B1 | 1/2006 | Beatty et al. |
| 7,288,104 B2 | 10/2007 | Heil, Jr. |
| 2001/0012918 A1 | 8/2001 | Swanson |
| 2002/0029783 A1 | 3/2002 | Stevens et al. |
| 2004/0181139 A1 | 9/2004 | Falwell et al. |
| 2004/0225304 A1 | 11/2004 | Vidlund et al. |

(Continued)

OTHER PUBLICATIONS

"About the CorCap Cardiac Support Device", *Acorn Cardiovascular* (tm) web site; http://www.acorncv.com/patients_families/corcap.cfm, (Published on or before Aug. 26, 2003),4 pgs.

(Continued)

*Primary Examiner*—John P Lacyk
(74) *Attorney, Agent, or Firm*—Schwegman, Lundberg & Woessner, P.A.

(57) ABSTRACT

A splint assembly includes an elongate body. An active fixation fastener is coupled substantially adjacent to a distal end of the elongate body. The splint assembly includes at least one flange coupled to the elongate body proximal the active fixation fastener. In one option, a stop of the at least one flange projects outside of an outer perimeter of the elongate body. In another option, the active fixation fastener is spaced from the at least one flange where the active fixation fastener and the at least one flange pull at least one heart chamber toward a substantially unexpanded shape when in an implanted condition within the heart an artery or a vein. In yet another option, the elongate body includes a predetermined curvature along at least a portion of the elongate body between the active fixation fastener and the at least one flange.

25 Claims, 7 Drawing Sheets

U.S. PATENT DOCUMENTS

2005/0288613 A1  12/2005  Heil

OTHER PUBLICATIONS

"U.S. Appl. No. 10/877,905 Non-Final Office Action Mailed Dec. 01, 2006", 12 Pages.

"U.S. Appl. No. 10/877,905 Notice of Allowance mailed Jun. 19, 2007", 4 Pages.

"U.S. Appl. No. 11/877,905 Response filed Apr. 2, 2007 to Non-Final Office Action Mailed Dec. 1, 2006", 12 Pages.

"Myosplint System", *Myocor* (r) Inc. web site; http://www.mycor.com/technology/myosplinttech.php, (Published on or before Aug. 26, 2002), 1 pg.

McCarthy, M.D., P. M., et al., "Device-Based Change in Left Ventricular Shape: A New Concept for the Treatment of Dilated Cardiomyopathy", *Journal of Thoracic and Cardiovascular Surgery*, 122(3), (2001), 482-490.

ENDOCARDIAL SPLINT AND METHOD THEREFOR

CROSS-REFERENCE TO RELATED APPLICATION

This application is a continuation of U.S. application Ser. No. 10/877,905, filed on Jun. 25, 2004 now U.S. Pat. No. 7,288,104, which is incorporated herein by reference.

TECHNICAL FIELD

This relates generally to splints to retain the heart in a desired shape and in particular to an endocardial splint implant couplable to the inner surfaces of a heart and/or surrounding vasculature.

BACKGROUND

Patients suffering from heart failure often experience enlarging of the heart. Increase in the heart size imposes stresses on the heart walls. Such increased stress aggravates the heart failure and causes the condition to worsen and correspondingly enlarges the heart further. Additional enlargement of the heart compounds the stress on the heart walls and repeats the pattern. Preventing enlargement of the heart reduces wall stress and minimizes the undesired increase in heart size.

In an attempt to address enlargement of the heart, socks positionable around the outer surface of the heart have been developed. The sock is constructed from elastic fabric mesh filaments. The sock is designed to constrain enlargement of the heart by absorbing some of the stress in the heart walls. One disadvantage of this type of device is the need for extensive surgical intervention to implant the device around the outer surface of the heart. Implantation includes separation of the sternum and opening of the chest by spreading the ribs.

Additionally, splints have been designed to traverse chambers of the heart, extend through the walls, and anchor on the heart outer surface. Multiple splints are fed through a chamber and fastened to the outer surface of the heart. Using this device, like the mesh sock described above, requires extensive open chest surgery. Additionally, neither of these designs provides means for applying electrical resynchronization and/or defibrillation therapy to the heart.

What is needed is an endocardial splint assembly that overcomes the shortcomings of previous designs. What is further needed is an endocardial splint assembly that is implantable without requiring open chest surgery.

SUMMARY

A splint apparatus for substantially preventing or reducing enlargement of the heart includes an elongate body, and at least one flange coupled around at least a portion of the elongate body. In one example, the at least one flange includes at least one stop extending outside an outer perimeter of the elongate body. An active fixation fastener is coupled to a distal end of the elongate body. In another example, the active fixation fastener is spaced from the at least one flange where the active fixation fastener and the at least one flange pull at least one heart chamber toward a substantially unexpanded shape when in an implanted condition within the heart, an artery or a vein.

Several options for the splint apparatus follow. In one option, at least a portion of the active fixation fastener has a textured surface. In another option, at least a portion of the at least one flange has a textured surface. In yet another option, at least a portion of the elongate body between a position proximal to the at least one flange and the active fixation fastener has a textured surface. In one example, the elongate body has a predetermined curvature along at least a portion of the elongate body between the active fixation fastener and the at least one flange. The elongate body, in another example, includes a shape memory material along at least the portion of the elongate body between the active fixation fastener and the at least one flange. In yet another example, the at least one flange is spaced from the active fixation fastener so the at least one flange is spaced from the active fixation fastener so when in the implanted condition the at least one flange is substantially adjacent to a septal wall disposed between a right ventricle and a left ventricle when the active fixation fastener is implanted in the inner surface of a left ventricle wall. The splint apparatus includes a second flange, in one option, coupled to the elongate body and proximal to the at least one flange. Optionally, the second flange is spaced from the active fixation fastener so the second flange is substantially adjacent to a vein. In another option, the stop includes an annular ridge extending substantially around the outer perimeter of the elongate body. In one example, the at least one flange is slidably coupled to the outer perimeter of the elongate body. The at least one flange is deformable, in another example, and an inner surface of the at least one flange grasps the outer perimeter of the elongate body in a deformed condition. The active fixation fastener includes a helix projection in yet another option.

A method for implanting a splint apparatus includes inserting an elongate body through a vein or artery. A distal end of the elongate body is advanced into a heart chamber. The distal end of the elongate body is coupled to an inner surface of the heart. At least one flange is coupled to the inner surface of the heart, artery, or vein so at least a portion of the elongate body traverses the heart chamber. In one example, the at least one flange is coupled to the elongate body proximal the distal end. At least the portion of the elongate body that traverses the heart chamber is tensioned to substantially prevent or reduce enlargement of the heart.

Several options for the method follow. In one option, the distal end of the elongate body is coupled to the inner surface of the heart by coupling an active fixation fastener to the inner surface of the heart. In another option, coupling the at least one flange to the heart, artery or vein includes disposing the at least one flange within a puncture in the heart, artery or vein. Coupling the at least one flange to the heart, artery or vein includes, in yet another option, engaging the at least one flange against a septal wall of the heart. In one example, the at least one flange seals around a puncture of the septal wall. In another example, engaging the at least one flange against the septal wall includes using low and/or high pressure to draw and/or press the flange against the septal wall. In another option, tensioning at least the portion of the elongate body that traverses the heart chamber includes moving the at least one flange along the elongate body and immobilizing the at least one flange on the elongate body. Where the at least one flange is deformable, in one example, immobilizing the at least one flange includes suturing tissue around the at least one flange to deform the at least one flange and grasp the elongate body. In still another option, tensioning at least the portion of the elongate body that traverses the heart chamber includes removing a stylet disposed within the elongate body. Optionally, tensioning with a predisposed curvature of the elongate body tensions at least the portion of the elongate body that traverses the heart chamber. In yet another example, the method further includes providing electrical stimulation to the heart through the elongate body.

The above described endocardial splint assembly allows for implantation without extensive open chest surgery. In one example, the endocardial splint assembly is inserted through a puncture in a heart, artery or vein and implanted in a chamber of the heart. In another example, insertion and implantation of the endocardial splint assembly are accomplished with a stylet and maneuvering of the splint assembly through the heart and vasculature. As a result, implantation of the endocardial splint assembly does not require extensive surgical measures including spreading of the ribcage.

The splint apparatus substantially prevents or reduces enlargement of the heart due to increased heart stress by applying a tension through the splint apparatus. The splint apparatus is useful for preventing future heart enlargement and for reducing enlargement already present. In one example, the tension is transmitted to the heart tissue through the active fixation fastener at the splint apparatus distal end. In another example, the splint apparatus includes textured surface to promote scar tissue ingrowth. In one option, the ingrown scar tissue distributes the tension in the splint apparatus to a larger area of the heart thereby constraining additional heart tissue from enlarging. In another option, the tension is applied between the flange disposed along the elongate body and the active fixation fastener. In yet another option, tension is applied between the active fixation fastener and an intermediate portion of the elongate body through a predetermined curvature of the elongate body. Optionally, multiple splints are implanted within the heart to compound the tension applied to the heart tissue. In another example, multiple splints are implanted to substantially prevent enlargement of the heart in varying locations in the heart.

Furthermore, the less invasive surgery used with the endocardial splint assembly provides an effective, low cost alternative to open chest surgery. Additionally, in another example, the endocardial splint assembly is used for delivering electrical stimulation to the heart in the option including a conductor within the elongate body. In one option, the application of electrical stimulation through the endocardial splint assembly condenses a stimulation lead and splint assembly into one compact device. Further, a single procedure is performed to implant the endocardial splint assembly that delivers stimulation therapy to the heart instead of two surgeries for implanting a splint assembly and a stimulation lead.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims and their equivalents.

DESCRIPTION OF THE EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Figure 1:
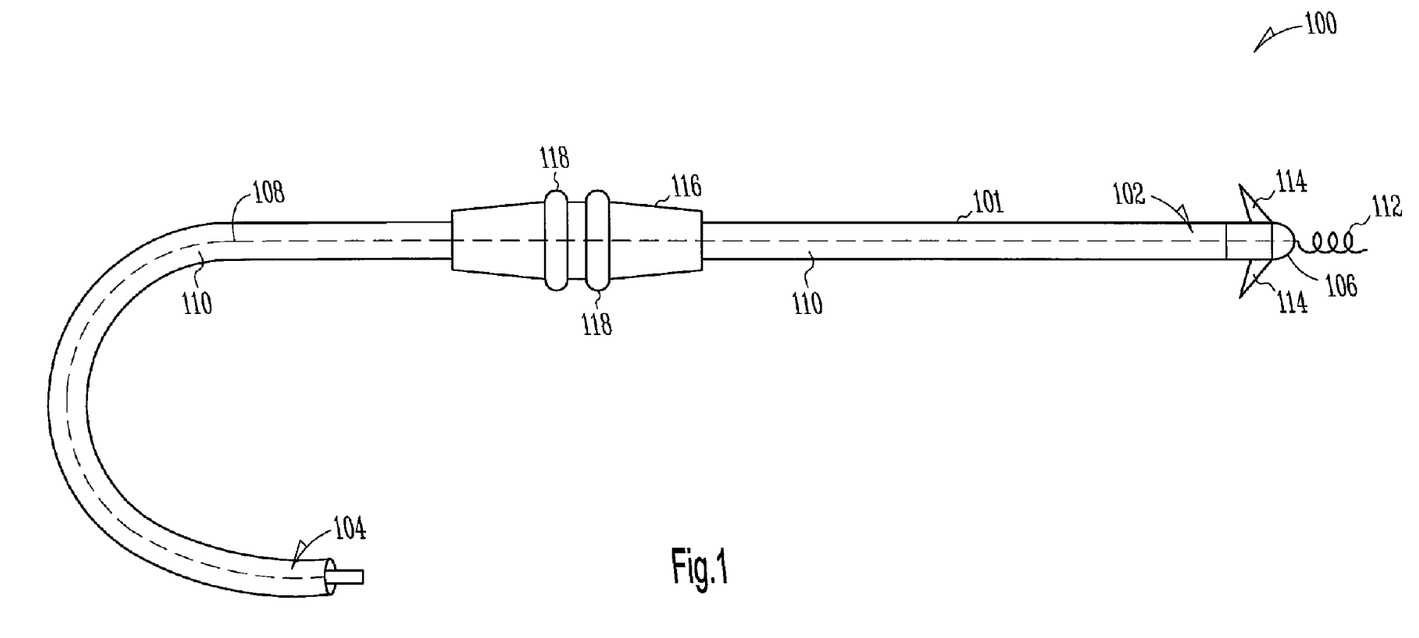
FIG. 1 is a top view of splint apparatus constructed in accordance with one embodiment.

FIG. 1 is a top view of a splint apparatus 100 for constraining undesired enlargement of the heart. The splint apparatus 100 includes an elongate body 101 having a distal end 102 and a proximal end 104. In one example, the splint apparatus 100 is an implantable lead assembly. In one option, the distal end 102 includes at least one electrode 106 which electrically couples the splint apparatus 100 with a heart. In another option, the electrode 106 can be a unipolar type electrode. In yet another option, the elongate body 101 includes at least one additional electrode, thereby providing a bipolar or multipolar configuration. Optionally, at least one electrical conductor 108, as shown in phantom lines in FIG. 1, is disposed within the splint apparatus 100. The at least one electrical conductor 108 electrically couples the electrode 106 with the proximal end 104 of the splint apparatus 100. In another option, the splint apparatus 100 includes multiple conductors 108 electrically coupled to multiple corresponding electrodes 106.

Figure 2:
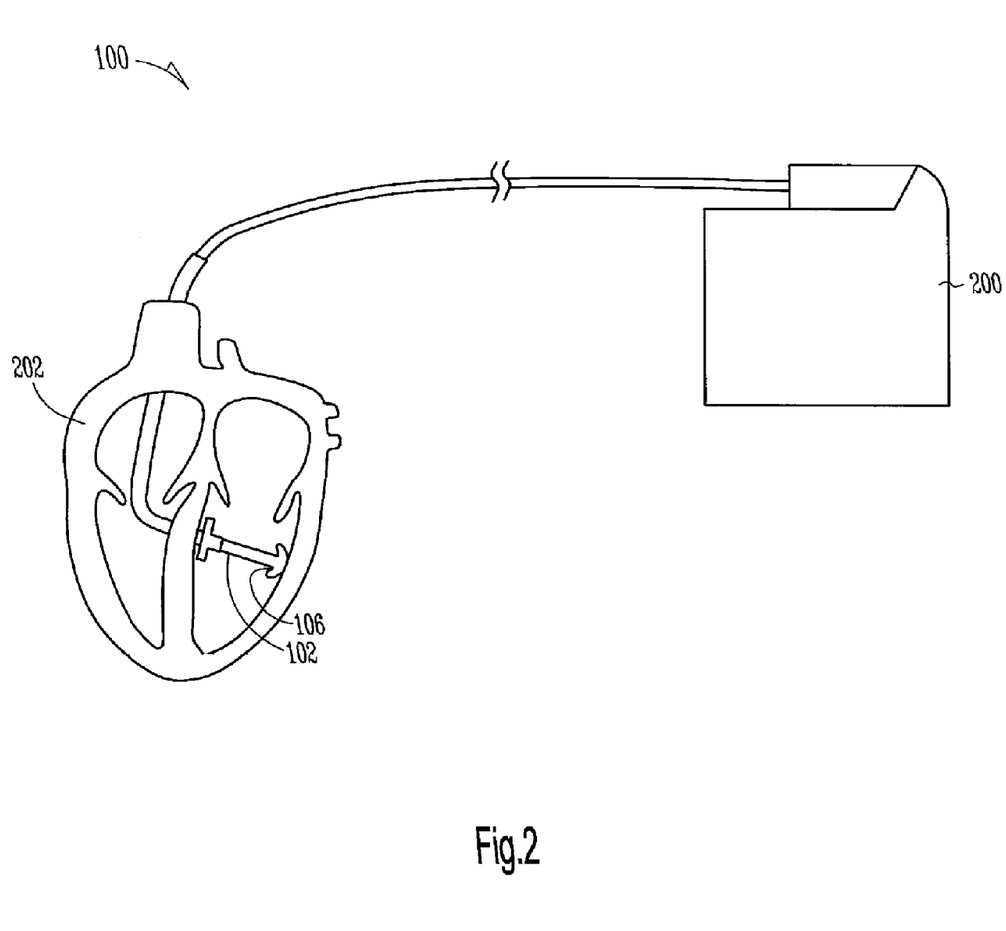
FIG. 2 is a schematic diagram of a splint apparatus system including a lead for use with a heart constructed in accordance with one embodiment.

FIG. 2 is a schematic diagram of one example of the splint apparatus 100 coupled to a pulse generator 200. The distal end 102 of the splint apparatus 100 is disposed within a heart 202. The pulse generator 200 includes a source of power as well as an electronic circuitry portion. In one option, the pulse generator 200 is a battery-powered device which generates a series of timed electrical discharges or pulses used to initiate depolarization of excitable cardiac tissue. The pulse generator 200 is generally implanted into a subcutaneous pocket made in the wall of the chest. Alternatively, the pulse generator 200 can be placed in a subcutaneous pocket made in the abdomen, or in other locations. In one option, the electrical conductor 108 carries electrical current and pulses between the pulse generator 200 and the electrode 106.

Referring again to FIG. 1, in one option, the elongate body 101 includes an insulating layer 110 formed of a biocompatible polymer suitable for implementation within the human body. The insulating layer 110 is made from a silicone rubber type polymer, in one option. In another option, the insulating layer 110 includes polyurethane. In yet another option, the insulating layer 110 includes polyethylene terephthalate (PTFE). In still another option, the insulating layer 110 includes ethylene-tetrafluoroethylene (ETFE), or polysiloxane urethane. In the example where the splint apparatus includes the conductor 108, the insulating layer 110 surrounds and insulates the conductor 108.

An active fixation fastener 112, for instance a helix projection, is coupled to the distal end 102 of the splint apparatus 100. In another option, the active fixation fastener 112 includes a barbed projection, a hook or the like. The active fixation fastener 112 couples the distal end 102 to an inner surface of the heart. The active fixation fastener 112 is optionally electrically coupled with the conductor 108. In one option, the active fixation fastener 112 delivers pulses from the pulse generator 200 to the heart 202 (FIG. 2). In another option, tines 114 extend from the elongate body 101. In one example, the tines 114 are electrically coupled to the electrode 106.

At least one flange 116 is coupled to the elongate body 101. The flange 116, in one example, is a jacket that at least partially surrounds the elongate body 101 and has an outer perimeter larger than the outer perimeter of the elongate body 101. In another example, the flange 116 includes a clamp, clip or the like. In one option, the flange 116 is slidably coupled to the elongate body 101. In another option, the flange 116 is integral to the elongate body 101. The flange 116 includes a biocompatible polymer (e.g. silicone), in one example, and is deformable.

Force applied around the flange 116 deforms the flange and the elongate body 101 is grasped by the deformed flange 116. Optionally, deformation of the flange 116 immobilizes the flange 116 along the elongate body 101 preventing movement of the flange 116 relative to the elongate body 101. In one option, suturing or clamping of tissue surrounding the flange 116 (e.g. heart, artery or vein tissue) deforms the flange 116 and causes it to grasp the elongate body 101. In another option, the flange 116 is deformed with a clamp or the like crimped around the flange 116. Where the flange 116 is a clamp, clip or the like, as described above, coupling of the flange 116 to the elongate body 101 immobilizes the flange 116 along the elongate body 101.

In another option, the flange includes at least one stop 118, for instance an annular ridge. In the example shown in FIG. 1, the flange 116 includes two stops 118, both of which are two annular ridges. A corresponding annular groove lies between the two stops 118. In yet another option, the stop 118 is a projection, a stud, knurled surface, or the like. The at least one stop 118 engages surrounding tissue, optionally, thus seating the at least one stop 118 against surrounding tissue. In still another option, surrounding tissue from around a puncture formed in the heart, vein, or artery is retained in the annular groove between two stops 118, as described above. The flange 116, optionally, has a cross sectional area larger than the area of the puncture. The flange 116 creates an interference fit between the splint apparatus 100 and the surrounding tissue, in one example. In another option, the stop 118 enhances the interference fit between the splint apparatus 100 and surrounding tissue by increasing the friction at the interface between the flange 116 and the tissue. In still another option, the interference fit between the flange 116 and the surrounding tissue substantially cooperates with deformation of the flange 116 to immobilize at least a portion of the splint apparatus 100.

In yet another option, the splint apparatus 100 includes passive fixation features, such as texturing, to promote tissue ingrowth from the surrounding heart, arteries and/or veins. The texturing includes, but is not limited to, knurled, porous, roughened surfaces or the like. In one option, the texturing is provided by a porous mesh. After implantation, the initial protein and platelet deposition on the textured surface is replaced by fibrotic "scar" tissue extending to the heart, arteries and/or veins. A roughened or textured surface provides the substrate to firmly anchor the splint apparatus 100 to the surrounding tissues by means of scar tissue ingrowth. Scar tissue replaces the platelets over time to cover the splint apparatus 100 and more tightly anchor the splint apparatus 100 to the heart, arteries and/or veins. In another example, development of the scar tissue decreases the likelihood of blood clotting within the heart and the related dangers of embolization of those clots to the body, including the brain (i.e., stroke). In one option, the active fixation fastener 112 includes texturizing. Scar tissue ingrowth around the active fixation fastener 112 tightly couples the active fixation fastener 112 to the heart 202 (See FIG. 2). Further, scar tissue ingrowth around the active fixation fastener 112 distributes tension forces transmitted along the splint apparatus to the active fixation fastener 112 and across the ingrown heart scar tissue. Without scar tissue ingrowth around active fixation fastener 112, tension forces are focused at the initial point of coupling between the active fixation fastener 112 and the heart 202. Sufficient tension without scar tissue ingrowth can cause dislodging of the active fixation fastener 112 from the heart 202. Optionally, the electrode 106 and/or tines 114 are texturized to promote scar tissue growth near the distal end 102 of the splint apparatus 100. In another option, the flange 116 includes texturizing to promote scar tissue ingrowth and corresponding tight coupling between the flange 116 and the tissue surrounding the flange 116. In yet another option, the elongate body 101 is texturized to promote scar tissue ingrowth along the elongate body 101. In one example, the elongate body 101 is texturized from a point just proximal to the flange 116 to the distal end 102. The texturized portion of the elongate body 101 acts as a passive fixation feature.

Figure 3:
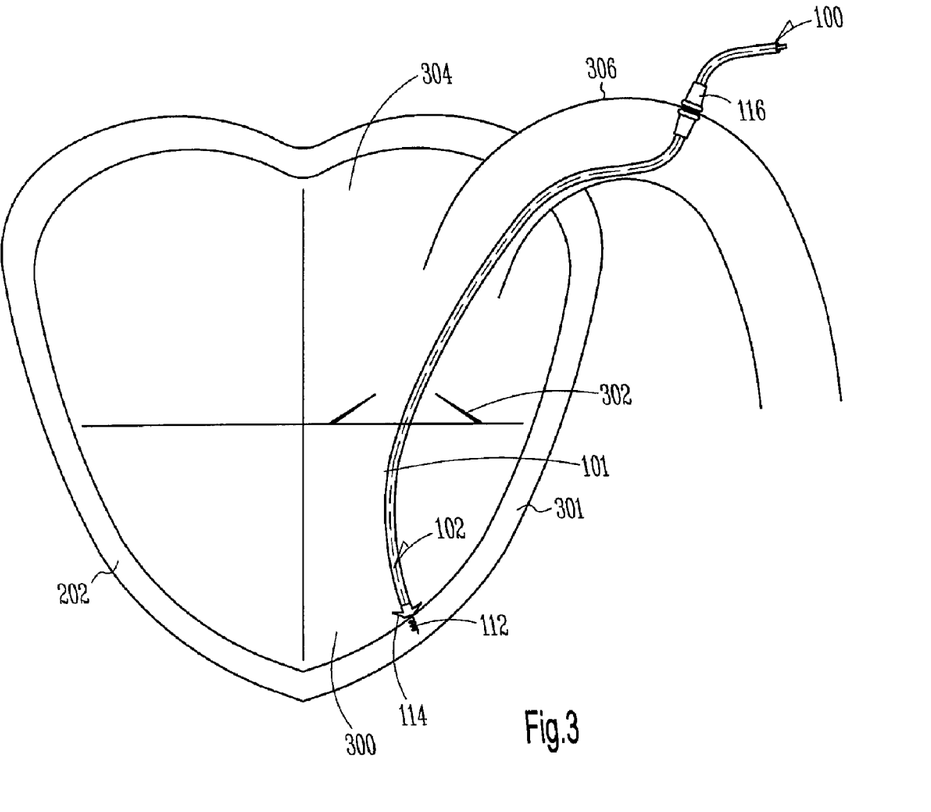
FIG. 3 is a sectional view of a heart showing a splint apparatus constructed in accordance with one embodiment.

FIG. 3 is a sectional view of the heart 202 showing one example of the splint apparatus 100 implanted therein. The active fixation fastener 112 is coupled with an inner surface 301 that defines a left ventricle 300 (i.e. the endocardial surface of the left ventricle). In one option, the tines 114 are coupled with naturally occurring fibrous tissue extending from the inner surface 301 to float within the left ventricle 300. The elongate body 101 traverses the left ventricle 300 and extends through the mitral valve 302 into a left atrium 304. The flange 116 is coupled to the wall of an aorta 306, another portion of the heart 202 or the like. In another option, suturing or the like is performed around the flange 116. As described above, the suturing deforms the flange 116 and the flange 116 grasps the elongate body 101. Deformation of the flange 116 immobilizes it along the elongate body 101. In yet another option, by immobilizing the flange 116, the flange 116 is selectively spaced from the active fixation fastener 112. The flange 116 is selectively spaced from the active fixation fastener 112, in still another option, so force later applied by the heart when attempting to expand will put the elongate body 101 in tension between the active fixation fastener 112 and the flange 116. The tension in the splint apparatus 100 substantially prevents the heart 202 from expanding due to increased stresses caused, for instance, by congestive heart failure. Optionally, the splint apparatus 100 retains the heart 202 in a substantially unexpanded shape when the splint apparatus 100 is in tension. In a condition where the heart 202 has already experienced expansion, the tension in the splint apparatus 100 reduces the enlargement. The flange 116 is spaced from the active fixation fastener 112 so tension within splint apparatus 100 is transmitted through the active fixation fastener 112 to the heart tissue. In one option, the tension in the splint apparatus 100 substantially prevents enlargement of the left ventricle 300. In another option, the flange 116 is coupled to another portion of the heart, an artery or a vein and the active fixation fastener 112 is coupled to the endocardium of the left ventricle 300 or a different endocardial surface of the heart (e.g. the right ventricle).

In another option, prior to deformation and immobilization of the flange 116, the flange 116 is interference fit within the tissue of the aorta 306. While interference fit, the flange 116 is translated along the elongate body 101 toward the distal end 102 and the active fixation fastener 112. The flange 116 is positioned along the elongate body 101 so the splint apparatus 100 is in tension between at least the flange 116 and the active fixation fastener 112. The tissue surrounding the flange 116 is then sutured or clamped so the flange 116 grasps the elongate body 101 to immobilize the flange 116 with respect to the elongate body 101. The tension in the splint apparatus 100 is transmitted along the elongate body 101 to the distal end 102 to counter and substantially prevent or reduce enlargement of the heart 202. Optionally, splint apparatus 100 retains the heart 202 in a substantially unexpanded shape when the splint apparatus 100 is under tension.

Figure 4:
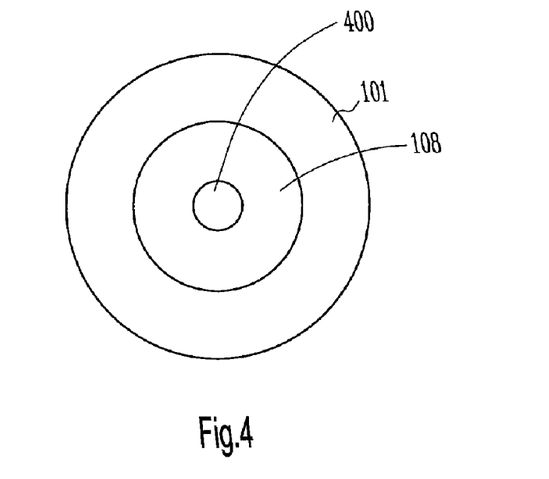
FIG. 4 is a sectional view of a splint apparatus constructed in accordance with one embodiment.

FIG. 4 is a sectional view of the elongate body 101. As described above, in one option, the elongate body 101 includes an electrical conductor 108. Optionally, the electrical conductor 108 is a coil wound substantially around the longitudinal axis of the elongate body 101. In another option, the coiled conductor 108 includes a lumen 400 extending from the proximal end 104 of the elongate body 101 to the electrode 106 (See FIG. 1). In one example, the lumen 400 is dimensioned and configured to slidably receive a stylet, or guidewire. The stylet, in yet another option, is fed into the lumen 400 to straighten and stiffen the elongate body 101. The stylet is used, in one option, to guide and implant the stiffened splint apparatus 100 in the heart, arteries, and or veins. Optionally, once the splint apparatus 100 is implanted, the stylet is removed so a predetermined curvature of the splint apparatus 100 pulls the active fixation fastener 112 and distal end 102 toward an intermediate portion of the elongate body 101 between the distal end 102 and the proximal end 104, as described herein.

Figure 5:
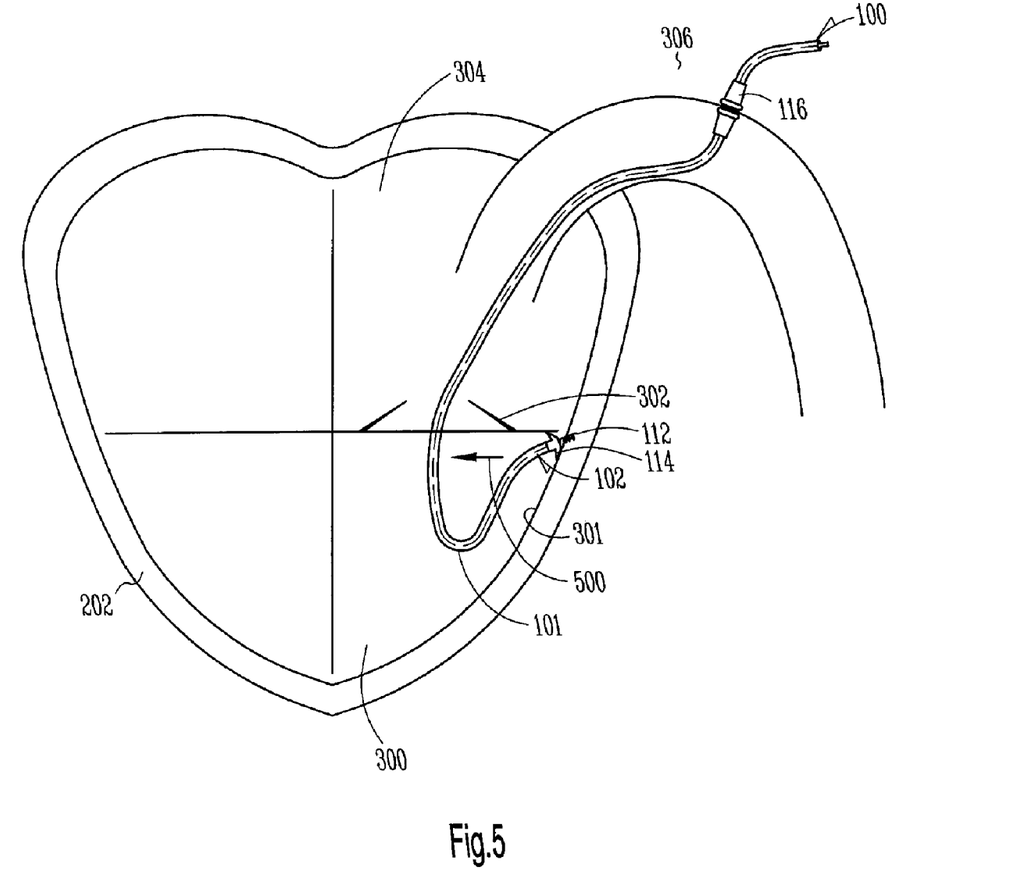
FIG. 5 is a sectional view of a heart showing a splint apparatus constructed in accordance with another embodiment.

FIG. 5 is a sectional view of the heart 202 showing another example of the splint apparatus 100 implanted therein. In one option, the active fixation fastener 112 is coupled with an inner surface 301 of the wall of the left ventricle 300 (i.e. the endocardial surface of the left ventricle). In one example, the active fixation fastener 112 is coupled substantially adjacent to the mitral valve 302. In another option, the flange 116 is coupled to the wall of the aorta 306. In yet another option, suturing is performed around the flange 116. As described above, the suturing deforms the flange 116 and the flange 116 grasps the elongate body 101. In one option, the flange 116 is immobilized on the elongate body 101 where it grasps the elongate body 101.

In another option, the elongate body 101 has a predetermined curvature (e.g., desired bend, bias or the like) shown in an intermediate portion of the elongate body 101 substantially adjacent to the distal end 102. The elongate body 101 includes, in one option, a shape memory material, for example, nitinol. The shape memory material is formed with the desired predetermined curvature and straightened prior to implantation. In another option, when implanted, the shape memory material is exposed to heat from the body, and the heat causes the elongate body 101 to assume the predetermined curvature. In yet another option, where the splint apparatus 100 includes the conductor 108 (FIG. 1), the conductor is intentionally twisted while forming the conductor 108 coil. In still another option, the outer surface of the elongate body 101 (e.g. insulating layer 110) is extruded and subsequently heated and formed with a predetermined curvature. Although this heating process applies to certain biocompatible polymers, for instance, polyurethane, other processes, such as simple molding, would be more appropriate for other polymers, for example, silicone rubber. The conductor 108, in another option, is stretched, bent or the like so as to impart a desired predetermined curvature. Twisting, stretching, bending, heating or the like of the conductor 108 induces curving of the elongate body 101 into a desired shape. Optionally, these methods of providing a predetermined curvature are combined so the outer surface of the elongate body 101 is extruded onto the preshaped coil of the conductor 108 and the outer surface is heated and formed with a predetermined curvature.

In yet another option, as described above, a stylet is inserted in the lumen 400 (See FIG. 4) for straightening of the splint apparatus 100 including the predetermined curvature. In operation, the splint apparatus 100, including a stylet disposed within the lumen 400, is implanted. The splint apparatus 100 is fed through a puncture in the aorta, in one option. In another option, the splint apparatus 100 is fed through a puncture in the heart, another artery, a vein, or the like. Optionally, the distal end 102 is inserted through the left atrium 304 and the mitral valve 302. The active fixation fastener 112, in one option, is implanted within an endocardial surface of the left ventricle 300. The stylet is removed from the lumen 400. Without the stylet, the splint apparatus 100, particularly the portion including the predetermined curvature is allowed to assume the curved geometry. In another option, removal of the stylet and subsequent exposure to body heat allows the splint apparatus 100 including nitinol to assume the curved geometry.

In one option, the curved geometry of the splint apparatus 100 pulls the distal end 102 toward an intermediate portion of the elongate body 101 between the flange 116 and the distal end 102. Arrow 500 shows the direction of pulling by the predetermined curvature. The curvature of the splint apparatus 100, in another option, has a radius that substantially prevents the elongate body 101 from tracking against an inner surface of a heart chamber (e.g. left ventricle 300) when the predetermined curvature pulls the distal end 102. In yet another example, where the distal end 102 is pulled toward the intermediate portion of the elongate body 101, the elongate body 101 proximal the distal end 102 is remote from the inner surface of a heart chamber. In one option, pulling of the distal end 102 tensions the elongate body 101 between the distal end 102 and the intermediate portion. In another option, the predetermined curvature pulls the distal end 102 and the heart tissue it is coupled to toward the intermediate portion of the elongate body 101. The pulling force exerted on the heart tissue counters and substantially prevents enlargement of the heart 202. Optionally, the pulling force provided by the predetermined curvature retains the heart 202 in a substantially unexpanded shape. The pulling force, in another option, reduces enlargement of the heart 202 where the heart 202 has already experienced expansion before implanting the splint apparatus 100.

In another option, a portion of the elongate body 101 adjacent to the distal end 102 has a textured roughened surface, as described above. The textured roughened surface is a passive fixation feature. In one option, fibrous scar tissue forms between the inner surface 301 of the left ventricle 300 and the elongate body 101 (e.g., an elongate body fixation length) and grows into the textured surface. The scar tissue forms fibrotic attachments to the inner surface 301 of the left ventricle 300 (e.g. the stable fibrous structures naturally lining the left ventricle 300). Scar tissue ingrowth around the elongate body 101 distributes the pulling force applied by the predetermined curvature over a larger area to provide more effective pulling of the endocardium of the left ventricle 300 to substantially prevent or reduce enlargement of the heart 202. Optionally, the scar tissue ingrowth assists in preventing dislodgement of the active fixation fastener 112 from the inner surfaces of the heart 202. In another option, the tines 114 assist in maintaining the engagement of the active fixation fastener 112 to the heart 202 inner surfaces.

Figure 6:
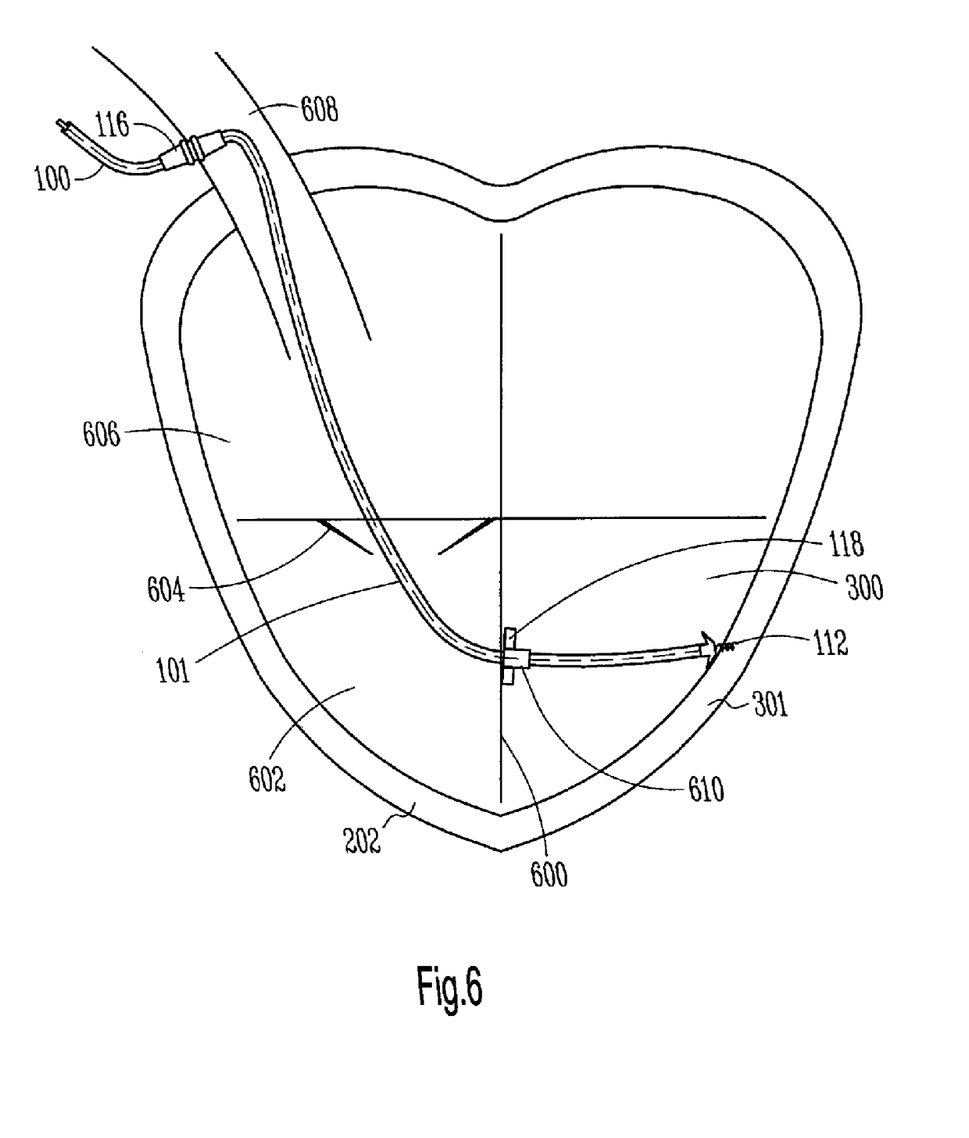
FIG. 6 is a sectional view of a heart showing a splint apparatus constructed in accordance with yet another embodiment.

FIG. 6 is another sectional view of the heart 202 showing another example of the splint apparatus 100 implanted therein. In one option, the active fixation fastener 112 is coupled to the inner surface 301 of the left ventricle wall (i.e. the endocardial surface of the left ventricle 300). In another option, the elongate body 101 traverses the left ventricle 300 and extends through a puncture (e.g., a septal opening) in the septal wall 600 between the left ventricle 300 and right ventricle 602. The elongate body 101 extends through the right ventricle 602, the tricuspid valve 604, and the right atrium 606. Optionally, the elongate body 101 is inserted into the vasculature through a puncture in the superior vena cava 608. A first flange 116 is disposed along the elongate body 101 and coupled to the tissue surrounding the puncture of the superior vena cava 608. In another option, a second flange 610 is coupled to the elongate body 101 and engaged against the tissue surrounding the puncture or opening in the septal wall 600. Optionally, the second flange 610, including stop 118 is seated against the septal wall 600.

In operation, the splint apparatus 100 is inserted through a puncture in the superior vena cava 608, in one option. In another option, the splint apparatus 100 is fed through the right atrium 606, right ventricle 602, and the left ventricle 300, for instance, through a septal opening. In yet another option, the second flange 610 is immobilized along the splint apparatus 100 and advanced with the apparatus 100 through the puncture in the superior vena cava 608 and the puncture in the septal wall 600 (e.g., the septal opening). In one option, feeding the second flange 610 through the septal opening of the septal wall 600 is unidirectional (i.e., one way). In one example, the second flange 610 deforms the tissue surrounding the puncture of the septal wall 600 to enter the left ventricle 300. After entrance the tissue assumes its original shape and the second flange 610, including the stop 118, seats against the septal wall 600. In another example, the stop 118 is at least one flexible flap that folds against the elongate body 101 as the second flange 610 is fed into the left ventricle 300. The flexible flap unfolds from the elongate body 101 within the left ventricle 300 so the second flange 610 seats against the septal wall 600.

As described above in other examples, the tissue surrounding the first flange 116 is sutured or clamped and deforms the first flange 116. Optionally, deformation of the first flange 116 causes the first flange 116 to grasp the elongate body to immobilize the first flange on the elongate body. In another option, the second flange 610 is molded around the elongate body 101, adhered to the elongate body, or interference fit on the elongate body, or the like. Optionally, the second flange 610 is immobilized along the elongate body 101. In one option, the high pressure of the blood flow through the left ventricle 300 presses the second flange 610 against the septal wall 600 and secures the second flange 610 against the septal wall 600. In another option, the second flange 610 seals around the puncture in the septal wall 600 and prevents cross blood flow between the left ventricle 300 and the right ventricle 602. In yet another option, the low pressure of the blood flow through the right ventricle 602 draws the second flange 610 against the septal wall 300 in the left ventricle 300 to secure the second flange 610 against the septal wall 600. In still another option, the low pressure provided from the right ventricle 602 and the high pressure from the left ventricle 300 cooperatively seal the second flange 610 around the puncture in the septal wall 600. Optionally, the second flange 610 includes a passive fixation feature, for instance, a textured surface to promote scar tissue ingrowth from the septal wall 600 to further secure the second flange 610 around the puncture.

In one option, the second flange 610 is spaced from the active fixation fastener 112 a predetermined distance. Where the heart 202 is under stress (caused for example by congestive heart failure) and attempts to enlarge, the splint apparatus is tensioned between the active fixation fastener 112 and the second flange 610, in one option. The spacing of the second flange 610 a predetermined distance from the active fixation fastener 112 ensures the splint apparatus 100 is in tension when the heart 202 experiences stresses that cause enlargement. The tension in the splint apparatus 100 is transmitted to the heart 202 through active fixation fastener 112 and surrounding ingrown scar tissue to substantially prevent or reduce enlargement of the heart 202.

Figure 7:
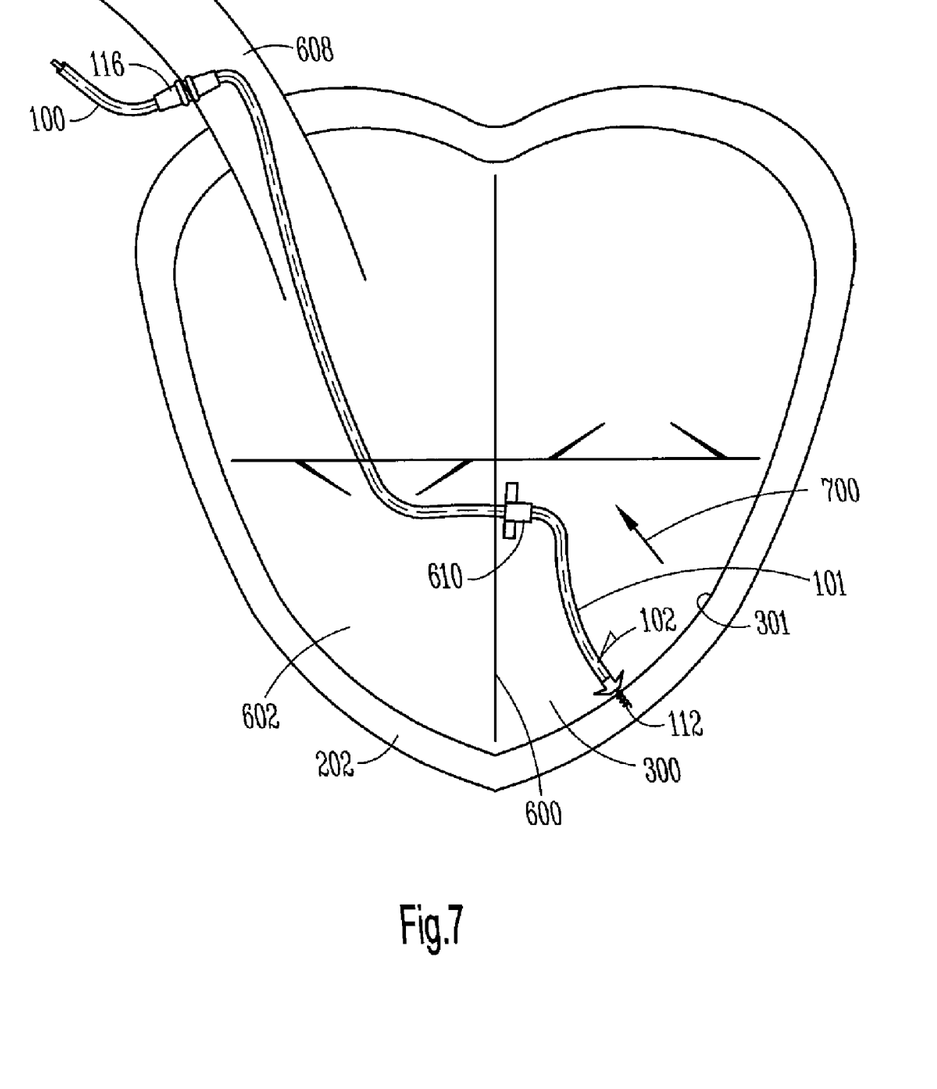
FIG. 7 is a sectional view of a heart showing a splint apparatus constructed in accordance with still another embodiment.

FIG. 7 is a sectional view of the heart 202 including yet another example of splint apparatus 100. In one option, the active fixation fastener 112 and the second flange 610 are disposed within the heart 202 similarly to the orientation shown in FIG. 6. Optionally, the second flange 610 is engaged against the septal wall 600 by low pressure from the right ventricle 602 and/or high pressure from the left ventricle 300. In another option, the first flange 116 is coupled to the superior vena cava 608.

In one option, an intermediate portion of the elongate body 101, between the second flange 610 and the distal end 102, has a predetermined curvature. In another option, the predetermined curvature pulls the distal end 102 in the direction of arrow 700. In one example, the predetermined curvature pulls the distal end 102 toward the intermediate portion of the elongate body 101. In still another option, pulling the distal end 102 applies a tension in the elongate body 101 between the distal end 102 and the intermediate portion. The predetermined curvature pulls the active fixation fastener 112 and the inner surface 301 of the left ventricle 300 it is coupled to toward the intermediate portion of the elongate body 101. The pulling force exerted on the heart tissue by the curved geometry of the splint apparatus 100 counters and substantially prevents enlargement of the heart 202. In yet another option, the second flange 610 is immobilized on the elongate body 101 a predetermined distance from the distal end 102 and the active fixation fastener 112. The second flange 610 substantially prevents undesirable translation of the elongate body 101 proximal to the second flange 610 into the left ventricle 300 when the intermediate portion assumes the curved geometry. Optionally, the second flange 610 maintains the desired spacing between the second flange 610 and the distal end 102 so the curved geometry pulls the heart tissue and substantially prevents or reduces enlargement of the heart 202.

In operation, in one option, the splint apparatus 100 is inserted in the heart in a similar manner as with the splint apparatus 100 shown in FIG. 6. The first flange 116 is optionally coupled to the superior vena cava 608. In another option, the second flange 610 is engaged against the septal wall 600. In yet another option, the active fixation fastener 112 is coupled to the inner surface 301 of the left ventricle 300 (i.e. the endocardium of the left ventricle). The splint apparatus 100, in still another option, is inserted through another vein, artery, or portion of the heart and coupled to various endocardial surfaces.

In another option, a stylet is removed from the lumen 400 (FIG. 4). Removal of the stylet allows the intermediate portion between the second flange 610 and the distal end 102 to assume the predetermined curvature. The predetermined curvature of the elongate body 101 pulls in the direction shown by the arrow 700. Optionally, the active fixation fastener 112 is pulled toward the intermediate portion, which in turn pulls the tissue of the left ventricle 300 toward the intermediate portion. The pulling motion caused by the predetermined curvature counters and substantially prevents or reduces enlargement of the heart 202. In another option, the active fixation fastener 112 and/or second flange 610 are textured to promote scar tissue ingrowth and further secure the splint apparatus 100 to the heart tissue. In yet another option, the elongate body 101 includes passive fixation features, for instance, texturing, to promote scar tissue ingrowth and decrease the likelihood of blood clotting thrombotic embolization around the splint apparatus 100, as described above.

Figure 8:
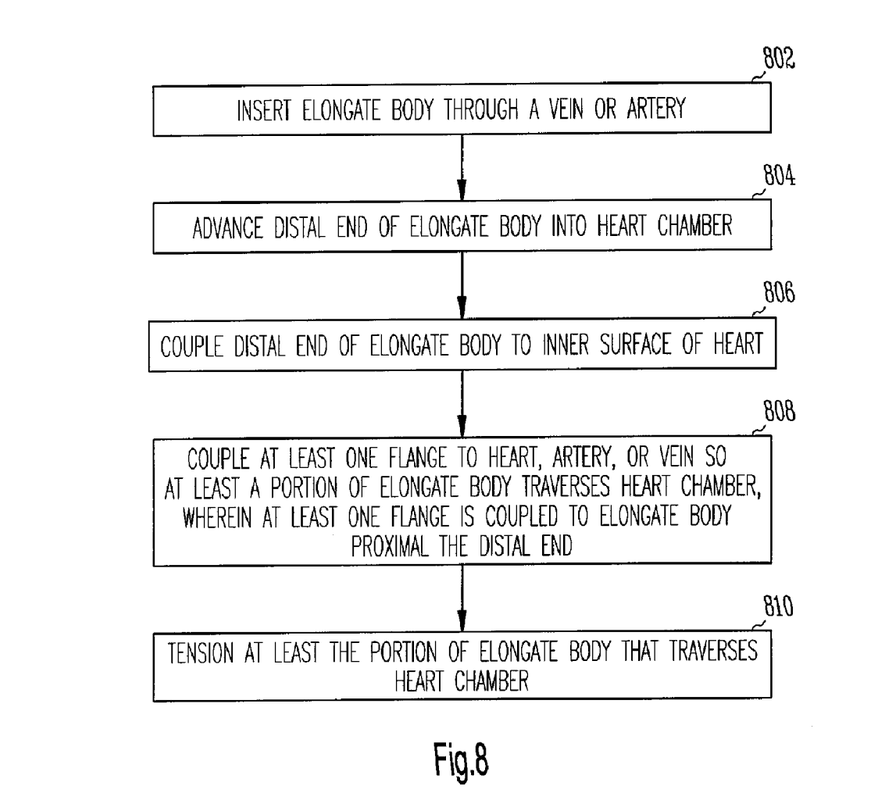
FIG. 8 is a block diagram showing one method of implanting a splint apparatus.

FIG. 8 is a block diagram illustrating a method 800 for using a splint apparatus. At 802, an elongate body is inserted through a vein or artery. At 804, a distal end of the elongate body is advanced into a heart chamber. At 806, the distal end is coupled to an inner surface of the heart (i.e. an endocardial surface of the heart). At 808, at least one flange is coupled to the inner surface of the heart, artery, or vein so at least a portion of the elongate body traverses the heart chamber. In one option, the at least one flange is coupled to the elongate body proximal the distal end. At 810, at least the portion of the elongate body that traverses the heart chamber is tensioned. Optionally, electrical stimulation is provided to the heart through the elongate body.

Several options for the method 800 follow. In one option, coupling the distal end of the elongate body to the inner surface of the heart includes coupling an active fixation fastener to the inner surface of the heart. In another option, the at least one flange is disposed within a puncture in the heart, an artery or a vein. Tensioning at least the portion of the elongate body that traverses the heart chamber, in another option, includes moving the at least one flange along the elongate body and immobilizing the at least one flange on the elongate body. Where the at least one flange is deformable, immobilizing the at least one flange includes suturing or clamping tissue around the at least one flange to deform the at least one flange and grasp the elongate body, in yet another option.

In still another option, the at least one flange is engaged against a septal wall of the heart, where the at least one flange seals around a puncture of the septal wall (e.g., a septal opening). Low and/or high pressure draws and/or presses the flange against the septal wall, in another option. Optionally, the at least one flange includes a stop (e.g. an annular ridge) extending substantially around the at least one flange. In one example, the annular ridge engages against the septal wall.

A stylet is disposed within the elongate body, in another option, and removed to tension at least the portion of the elongate body that traverses the heart. For instance, removal of the stylet permits the elongate body having a predisposed curvature to assume such a curvature. In one option, the predisposed curvature pulls the distal end of the elongate body toward an intermediate portion of the elongate body.

Figure 9:
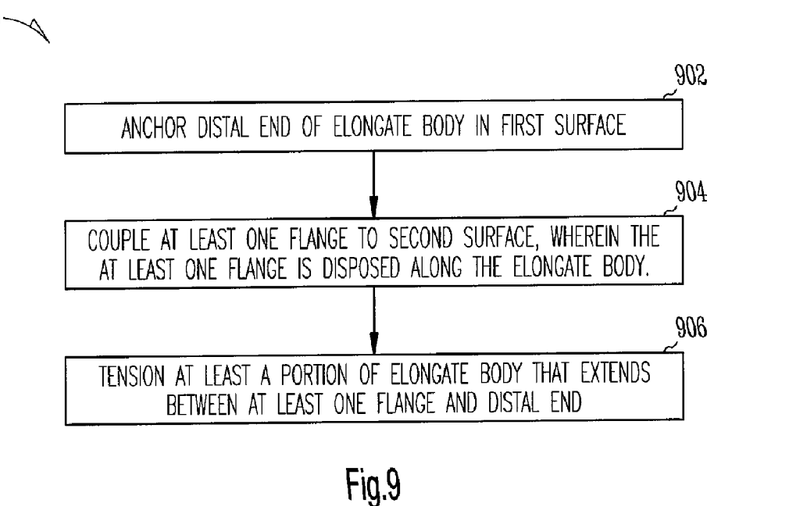
FIG. 9 is a block diagram showing one method of implanting a splint apparatus.

FIG. 9 is a block diagram illustrating a method 900 for using a splint apparatus. At 902, a distal end of an elongate body is anchored to a first surface, for instance the endocardium of a heart. In one option, the distal end includes an active fixation fastener (e.g. a helix projection) that is coupled to an inner surface of the heart. At 904, the at least one flange is coupled to a second surface (e.g. a vein, artery, another portion of the heart or the like). The at least one flange is disposed along the elongate body, for instance, proximal to the active fixation fastener and distal to a proximal end of the elongate body. In another option, coupling the at least one flange to a second surface includes disposing the at least one flange within a puncture in a heart, artery or a vein. Coupling the at least one flange to a second surface includes, in yet another option, engaging the at least one flange against a septal wall of the heart and the flange seals around a puncture in the septal wall. At 906, at least the portion of the elongate body that extends between the at least one flange and the distal end is tensioned. Tensioning of the portion of the elongate body includes, in still another option, moving the at least one flange along the elongate body. Removing a stylet disposed within the elongate body tensions the portion of the elongate body that extends between the at least one flange and the distal end, in another option. Optionally, tensioning of the portion of the elongate body extending between the at least one flange and the distal end includes tensioning with a predetermined curvature of the elongate body.

The method 900, in another option, includes constraining movement of at least one of the first surface or the second surface away from the other second or first surface. For instance, the method 900 constrains movement of a ventricular wall from a septal wall. In yet another option, the method 900 includes pulling at least one of the first or second surfaces toward the other of the second or first surfaces. Optionally, the method 900 includes providing electrical stimulation through a conductor disposed along the elongate body.

The above described endocardial splint apparatus allows for implantation without extensive open chest surgery. In one example, the endocardial splint assembly is inserted through a puncture in a heart, artery or vein and implanted in a chamber of the heart. In one option, insertion and implantation of the endocardial splint assembly are accomplished with a stylet and maneuvering of the splint assembly through the heart and vasculature. As a result, implantation of the endocardial splint assembly does not require extensive surgical measures including, for instance, spreading of the ribcage.

The splint apparatus substantially prevents or reduces enlargement of the heart due to increased heart stress by applying a tension through the splint apparatus. In one example, the tension is transmitted to the heart tissue through the active fixation fastener at the splint apparatus distal end. In another option, the splint apparatus includes passive fixation features, for example, a textured surface, to promote scar tissue ingrowth. The ingrown scar tissue distributes the tension in the splint apparatus to a larger area of the heart to constrain additional heart tissue from enlarging, in one option. The tension is applied, in another option, between the flange disposed along the elongate body and the active fixation fastener. In yet another option, tension is applied between the active fixation fastener and an intermediate portion of the elongate body (e.g., an elongate body fixation length) through a predetermined curvature of the elongate body. Multiple splints are implanted to substantially prevent or reduce enlargement of the heart in varying locations in the heart, in another option. The splint apparatus is useful for preventing future heart enlargement and for reducing enlargement already present.

Furthermore, the less invasive surgery used with the endocardial splint assembly provides an effective, lower cost alternative to open chest surgery. Additionally, in another example, the endocardial splint assembly is used for delivering electrical stimulation to the heart in the option including a conductor within the elongate body. The application of electrical stimulation through the endocardial splint assembly condenses a lead assembly and splint assembly into one compact device. Further, a single procedure is performed to implant the endocardial splint assembly that delivers stimulation therapy to the heart instead of two surgeries for implanting a splint assembly and a stimulation lead.

It is to be understood that the above description is intended to be illustrative, and not restrictive. Many other embodiments will be apparent to those of skill in the art upon reading and understanding the above description. It should be noted that embodiments discussed in different portions of the description or referred to in different drawings can be combined to form additional embodiments of the present application. The scope of the invention should, therefore, be determined with reference to the appended claims, along with the full scope of equivalents to which such claims are entitled.

What is claimed is:

1. A splint apparatus comprising:
    an elongate body having a proximal portion, distal portion and intermediate portion;
    at least one passive fixation feature disposed along at least one of the distal portion and intermediate portion, the passive fixation feature sized and shaped to couple the elongate body along a heart wall inner surface;
    an active fixation device coupled with the distal portion, the active fixation device sized and shaped to couple within a heart wall; and
    an elongate body fixation portion between the active fixation device and the passive fixation feature, the elongate body fixation portion sized and shaped to couple along a heart wall length in an implanted condition, the elongate body fixation portion configured to transmit pulling forces to the heart wall length, and pull the heart wall toward a substantially unexpanded shape when in the implanted condition.

2. The splint apparatus of claim 1, wherein the at least one passive fixation feature includes a tissue-in-growth surface.

3. The splint apparatus of claim 1, wherein the at least one passive fixation feature extends along a length of the elongate body fixation portion.

4. The splint apparatus of claim 1, wherein the at least one passive fixation feature includes a plurality of passive fixation features along the elongate body fixation portion.

5. The splint apparatus of claim 1, wherein the active fixation device includes a helical projection.

6. The splint apparatus of claim 1, wherein the elongate body includes a predetermined spring bias sized and shaped to pull the elongate body fixation portion and the heart wall length in the implanted condition.

7. The splint apparatus of claim 1, wherein the elongate body includes at least one electrode.

8. The splint apparatus of claim 7, wherein the at least one electrode is disposed along the elongate body fixation portion, and the at least one electrode is positioned along the heart wall length by the active fixation device and the passive fixation feature.

9. The splint apparatus of claim 1 further comprising a flange coupled along the elongate body, the flange sized and shaped to pass through a heart septal wall opening between the right ventricle and the left ventricle, the flange is sized and shaped to engage against the left ventricle septal wall and be held in place by high pressure from the left ventricle and relatively lower pressure in the right ventricle.

10. A method for shaping a heart comprising:
    specifying a heart wall portion that when pulled inwardly into the heart will achieve a desired unexpanded shape for a heart wall;
    inserting an elongate body through vasculature surrounding the heart;
    advancing a distal end of the elongate body into a heart chamber and into a heart inner surface adjacent to the heart wall portion;
    coupling an elongate body fixation length along the heart wall portion; and
    shaping the heart wall into the desired unexpanded shape, including pulling the elongate body fixation length coupled along the heart wall portion.

11. The method for shaping the heart of claim 10, wherein advancing a distal end of the elongate body into the heart chamber includes, engaging the distal end of the elongate body to the heart inner surface with an active fixation device.

12. The method for shaping the heart of claim 10, wherein coupling the elongate body fixation length along the heart wall portion includes coupling a passive fixation feature with the heart wall portion, and the passive fixation feature is positioned remotely proximal from the distal end.

13. The method for shaping the heart of claim 10, wherein coupling the elongate body fixation length along the heart wall portion includes coupling a passive fixation feature with the heart wall portion, and the passive fixation feature extends from a remote proximal position toward the distal end.

14. The method for shaping the heart of claim 10, wherein pulling the elongate body fixation length coupled along the heart wall portion includes distributing pulling forces along the heart wall portion with the elongate body fixation length.

15. The method for shaping the heart of claim 10, wherein coupling the elongate body fixation length along the heart wall portion includes coupling an electrode positioned along the elongate body fixation length along the heart wall portion.

16. The method for shaping the heart of claim 15, wherein coupling the electrode positioned along the elongate body fixation length includes positioning the electrode along the heart wall portion and fixing the electrode in place with an active fixation device and a passive fixation feature.

17. The method for shaping the heart of claim 16, wherein fixing the electrode in place with the active fixation device and the passive fixation feature includes promoting tissue-in-growth along the elongate body fixation length with a passive fixation feature having a textured surface.

18. The method for shaping the heart of claim 15, wherein shaping the heart into the desired unexpanded shape includes electrically stimulating the heart wall portion with the electrode.

19. A method for shaping a heart comprising:
    inserting an elongate body through vasculature surrounding the heart;
    advancing a distal end of the elongate body through a septal opening in a septal wall between a right ventricle and a left ventricle, the distal end advanced into a left ventricle inner surface;
    advancing a flange coupled along the elongate body and proximal to the distal end through the septal opening into the left ventricle; and
    retaining the flange against the septal wall along a left ventricle side to substantially prevent cross flow between the right ventricle and left ventricle, the flange retained against the septal opening by high pressure in the left ventricle and lower pressure in the right ventricle.

20. The method for shaping the heart of claim 19, wherein advancing the flange coupled along the elongate body includes advancing a flange having a stop coupled thereto, the stop allowing movement of the flange from the right ventricle to the left ventricle, the stop substantially preventing movement of the flange from the left ventricle to the right ventricle.

21. The method for shaping the heart of claim 20 wherein advancing the flange coupled along the elongate body includes advancing a flange having a folding stop, the folding stop folding along the elongate body while passing through the septal opening and unfolding within the left ventricle.

22. The method for shaping the heart of claim 19, wherein retaining the flange against the septal wall includes engaging the flange against the left ventricle side surrounding the septal opening.

23. The method for shaping the heart of claim 19 further comprising tensioning the elongate body between at least the flange and the distal end, tensioning pulling the heart into an unexpanded shape.

24. The method for shaping the heart of claim 23, wherein tensioning the elongate body includes spacing the flange from the distal end a specified length such that the specified length of the elongate body pulls the heart into the unexpanded shape when the flange is retained against the septal wall and the distal end is advanced into the left ventricle inner surface.

25. The method for shaping the heart of claim 19, retaining the flange against the septal wall includes retaining the flange against the septal wall with tissue-in-growth.

* * * * *